(12) United States Patent
West et al.

(10) Patent No.: US 6,595,960 B2
(45) Date of Patent: Jul. 22, 2003

(54) FLEXIBLE NEEDLE ASSEMBLY

(75) Inventors: Robert E. West, Basking Ridge, NJ (US); Michael A. DiBiasi, West Milford, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/833,325

(22) Filed: Apr. 12, 2001

(65) Prior Publication Data

US 2002/0151849 A1 Oct. 17, 2002

(51) Int. Cl.[7] ................................................ A61M 5/32
(52) U.S. Cl. ..................... 604/181; 604/272; 604/273; 604/240
(58) Field of Search ............................ 604/181, 273, 604/240, 264, 272

(56) References Cited

U.S. PATENT DOCUMENTS

| | | | |
|---|---|---|---|
| 2,034,294 A | * 3/1936 | Hein | ........................ 604/241 |
| 3,884,230 A | 5/1975 | Wulff | ........................ 128/221 |
| 3,976,078 A | 8/1976 | Toriello | ........................ 128/329 |
| 3,994,295 A | * 11/1976 | Wulff | ........................ 604/241 |
| 4,512,769 A | 4/1985 | Kozam et al. | ............... 604/209 |
| 4,878,904 A | * 11/1989 | Callaway | ..................... 604/272 |
| 5,405,330 A | * 4/1995 | Zunitch et al. | .............. 604/240 |
| 5,462,535 A | 10/1995 | Bonnichsen et al. | ......... 604/272 |
| 5,599,323 A | 2/1997 | Bonnichsen et al. | ......... 604/272 |
| 5,951,530 A | 9/1999 | Steengaard et al. | .......... 604/272 |
| 5,984,906 A | 11/1999 | Bonnichsen et al. | ......... 604/272 |

* cited by examiner

*Primary Examiner*—Patrick Brinson
(74) *Attorney, Agent, or Firm*—Alan W. Fiedler

(57) ABSTRACT

An apparatus and method of providing a flexible needle assembly for use with a medication delivery pen. The flexible needle assembly includes a needle cannula having proximal and distal points and a hub coupled to the needle cannula. The hub includes a flexible roof, or ball-and-socket arrangement, that permits the needle cannula to move about the centerline of the hub. The flexible roof can include one or more concentric ribs to enhance flexibility of the needle cannula about the centerline of the hub.

6 Claims, 6 Drawing Sheets

FLEXIBLE NEEDLE ASSEMBLY

FIELD OF THE INVENTION

This invention relates generally to the field of medication delivery systems and, more particularly, to flexible needle assemblies for use with medication delivery pens.

BACKGROUND OF THE INVENTION

Medication delivery pens, such as hypodermic syringes, are used for self-injection of precisely measured doses of medication and are widely used, for example, by diabetics to dispense insulin. Medication delivery pens may also be used to inject human growth hormone as well as other types of liquid medication into a patient.

A typical prior art medication delivery system includes a pen having a cartridge, a plunger and a needle assembly. The pen is typically fabricated from a plastic or polymer material and has generally a tubular structure that is approximately the dimensions of a conventional writing pen.

The cartridge, which contains a volume of liquid medication, is generally an elongated tube of glass or plastic that has a pierceable rubber septum extending across a distal end of the cartridge.

The plunger is used to urge the medication, which is stored in the cartridge, out of the distal end of the cartridge.

The needle assembly includes an elongated needle cannula having opposed proximal and distal portions. The cylindrical wall of a needle hub surrounds the proximal point on the needle cannula and includes an array of internal threads for engaging external threads on the neck of the pen cartridge retainer or an adaptor.

Syringe systems as disclosed in U.S. Pat. Nos. 5,599,323 (Bonnichsen et al.) and 5,462,535 (Bonnichsen et al.) relate to a syringe system having a pen shaped syringe with a cartridge containing insulin and an injection needle.

U.S. Pat. No. 5,951,530 (Steengaard et. al.) relates to an injection needle mounted in a needle hub fitting onto an injection device from which preset doses of medicine from a cartridge accommodated in the device is administered.

U.S. Pat. No. 3,884,230 (Wulff) relates to a flexible needle and guard device for a hypodermic syringe. The device includes a flexure tube interconnected between the syringe and the needle. However, the Wulff device has a flexible needle, rather than a flexible hub.

One disadvantage to conventional medication delivery pens as disclosed in the prior art is that some patients may have a tendency to inadvertently move or otherwise jitter the needle assembly while injecting the medication. This can cause pain and/or skin trauma because the piercing procedure is not as precise as possible.

Accordingly, there is a need in the art for an apparatus and method that reduce the pain and skin trauma associated with unintended motion of a needle assembly while injecting medication.

There is also a need for an apparatus and method that permit the needle cannula to move about the centerline of the hub of a needle assembly.

SUMMARY OF THE INVENTION

Accordingly, one embodiment of the present invention is directed to a needle assembly for use with a medication delivery pen. The needle assembly has a needle cannula with a proximal portion and a distal portion. A hub, to which the needle cannula is mounted, includes a flexible roof portion. The flexible roof portion permits the needle cannula to move about the centerline of the hub.

Another embodiment of the present invention is directed to a medication delivery system that includes a medication delivery pen and a cartridge containing medication. The cartridge is disposed within the medication delivery pen. A needle assembly is engageable with the cartridge and includes a needle cannula and a hub. The needle cannula has a proximal portion and a distal portion. The needle cannula is mounted to the hub, which includes a flexible roof portion, which permits the needle cannula to move about the centerline of the hub. Thus, the medication can flow through the needle cannula during an injection procedure.

Yet another embodiment of the present invention is directed to a method of operating a medication delivery system. The method includes attaching a needle cannula, which has a proximal portion and a distal portion, to a hub. The hub includes a flexible roof portion. Next, the proximal portion of the needle cannula is coupled to a cartridge containing medication. The cartridge within the medication delivery pen dispenses medication. The next step is to inject the distal portion of the needle cannula into a patient and deliver the medication into the patient. The flexible roof portion of the hub permits the needle cannula to move about the centerline of the hub.

Yet another embodiment is directed to a needle assembly in which the hub and cannula are disposed in a ball-and-socket relationship. This ball-and-socket relationship permits the cannula to rotate relative to the hub.

The invention will next be described in connection with certain exemplary embodiments; however, it should be clear to those skilled in the art that various modifications can be made without departing from the spirit or scope of the claims.

BRIEF DESCRIPTION OF THE DRAWINGS

The invention will be more clearly understood by reference to the following detailed description in conjunction with the accompanying drawings.

DETAILED DESCRIPTION OF THE INVENTION

The present invention relates to a needle assembly that compensates for unintended or inadvertent movement of a medication pen. The apparatus and method permit a needle cannula to move about the centerline of a hub of the needle assembly.

Figure 1:
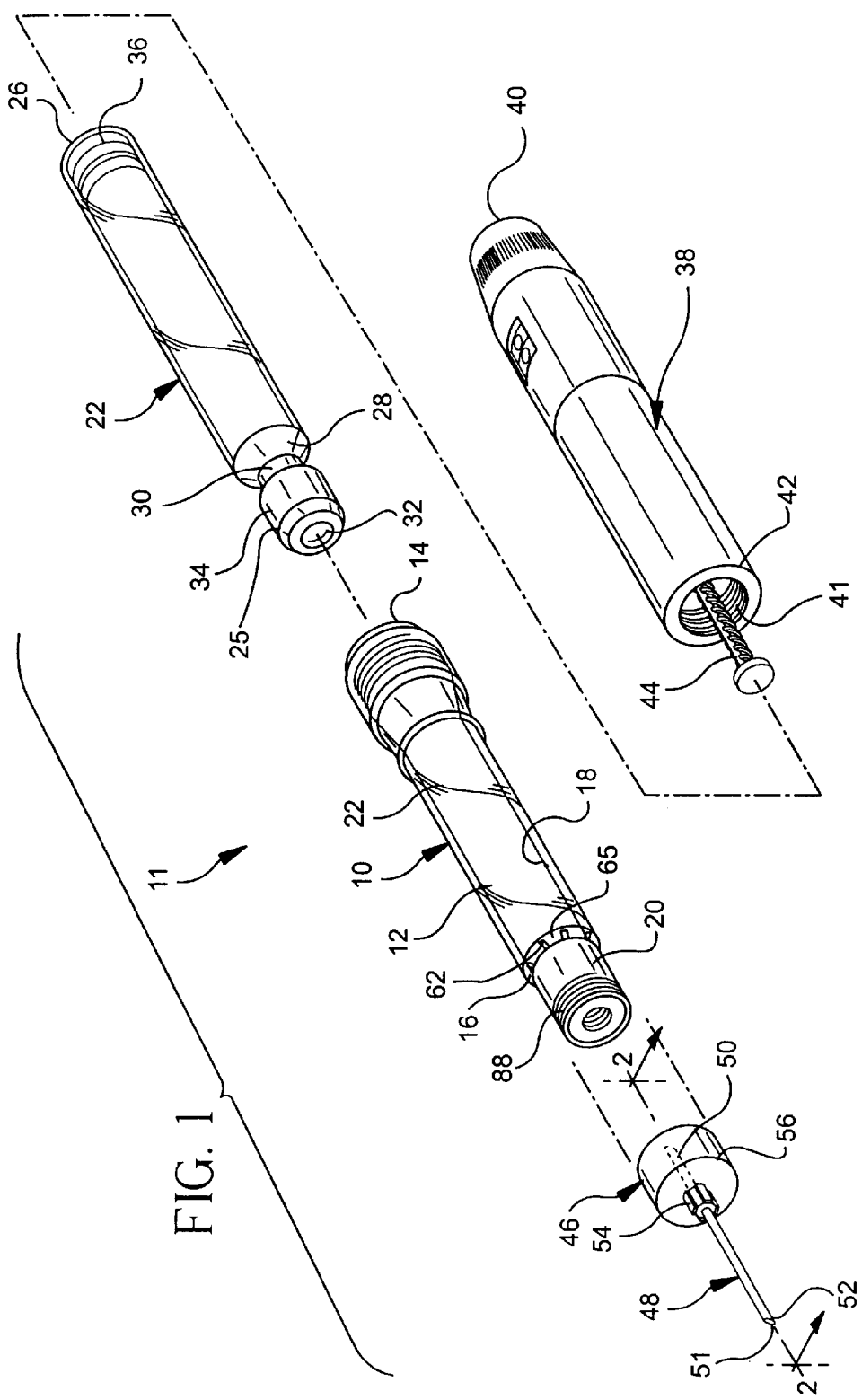
FIG. 1 is an exploded perspective view a medication pen in accordance with the present invention.

FIG. 1 shows a medication delivery pen 11 according to the present invention. A needle assembly is identified generally by the numeral 46. As shown in FIG. 1 medication delivery pen 11 includes a cartridge retainer assembly 10, a dosing apparatus 38 and a cartridge assembly 22. Needle assembly 46, as described in more detail below, is designed to be attached to a needle mounting insert tip 20 on cartridge retainer assembly 10.

Cartridge retainer assembly 10, as shown in FIG. 1 includes an elongate generally tubular body 12. A generally tubular needle mounting insert tip 20 is snap-fit mounted in distal end 16 of body 12 and cartridge retainer assembly 10 is dimensioned and configured to receive cartridge assembly 22 therein.

Cartridge assembly 22 includes an open proximal end 26 and a distal end 25, which is defined by an inwardly converging shoulder 28. A pierceable and resealable rubber septum 32 extends completely across the open distal end defined by neck 30. Rubber septum 32 is held in place by a metallic sleeve 34. Medication such as insulin, heparin or other liquid medication is pre-filled into cartridge assembly 22 and is retained therein by a rubber stopper 36. Stopper 36 is in sliding fluid-tight engagement with the tubular wall of cartridge assembly 22. Distally directed forces on stopper 36 urge the medication from pen 11.

Dosing apparatus 38 is generally cylindrical and includes opposed proximal and distal ends 40 and 42, respectively. Threads 41 are disposed at distal end 42 of dosing apparatus 38 for releasable threaded engagement with proximal end 14 of body 12 of cartridge retainer assembly 10. A plunger rod 44 projects distally from dosing apparatus 38 and is dimensioned to engage stopper 36 of cartridge assembly 22. Dosing apparatus 38 also includes known mechanisms for setting a selected dose of medication to be delivered by pen 11. A dispensing mechanism (not shown) is operative to drive plunger rod 44 a selected distance in a distal direction for moving stopper 36 a distance that will inject the selected dose of medication from cartridge assembly 22.

Needle assembly 46, according to the present invention, includes a needle cannula 48 with opposed proximal and distal tips 50 and 52, respectively, and a lumen 51 extending entirely therethrough. Needle cannulas having a gauge of approximately between 27 and 31 are typically used. The usable length of the needle cannula is typically between 0.157" (4 mm) and 0.394" (10 mm). Cannula 48 is either insert molded or retained with adhesive within cap or hub 56. Cap or hub 56 (referred to hub 56 herein) of needle assembly 46 includes an array of internal threads (not shown) for removably mounting needle assembly 46 to needle mounting insert tip 20 on cartridge retainer assembly 10 using external threads 88. Other releasable engagement means between needle assembly 46 and cartridge retainer assembly 10 can be provided. For example, external threads can be formed on needle assembly 46 and corresponding internal threads can be defined on cartridge retainer assembly 10 or a bayonet style mounting using lugs and slots can be used. In addition, needle assembly 46 could be "snap fit" on to cartridge retainer assembly 10. A support 54, such as cork, is used to secure needle cannula 48 to needle hub 56.

As shown in FIG. 1, body 12 of cartridge retainer assembly 10 includes a plurality of inwardly projecting supports 65 separated from one another by notches 62, wherein supports 65 are used to hold insert tip 20 in distal end 16 of cartridge retainer assembly 10.

Medication delivery pen 11 is used by mounting needle assembly 46 to needle mounting insert tip 20 of cartridge retainer assembly 10. This mounting is achieved by moving needle assembly 46 in a proximal direction over needle mounting insert tip 20 until the threads (not shown) of cap, or hub, 56 engage external threads 88 on needle mounting insert tip 20. Threads 88 of needle mounting insert tip 20 are spaced from the extreme distal end of needle mounting insert tip 20, therefore, the initial axial advancement of cap 56 over needle mounting insert tip 20 will cause proximal point 50 of needle cannula 48 to pierce rubber septum 32 of cartridge assembly 22 prior to rotational threaded engagement of needle assembly 46 with needle mounting insert tip 20. Thus, a bevel (not shown) that defines proximal point 50 will advance axially through septum 32 without a rotation that could tear rubber septum 32.

Use of medication delivery pen 11 proceeds in a conventional manner with dosing apparatus 38. Actuation of dosing apparatus 38 causes liquid medication in cartridge assembly 22 to be urged in a distal direction through lumen 51 of needle cannula 48. This distally directed liquid pressure also will cause septum 32 to distend in a distal direction. Septum 32 is spaced proximally from cork 54 of needle assembly 46, and will not be urged into contact with cork 54. Thus, drooling or weeping of liquid medication can be substantially prevented. This is enabled because cartridge assembly 22 is supported and accurately positioned by engagement of cartridge shoulder 28 on insert tip 20. Hence, neck 30 and crimped metallic sleeve 34 need not be closely engaged by needle mounting insert tip 20. After medication delivery pen 11 has been used, needle assembly 46 is separated from needle mounting insert tip 20 and discarded.

Figure 2:
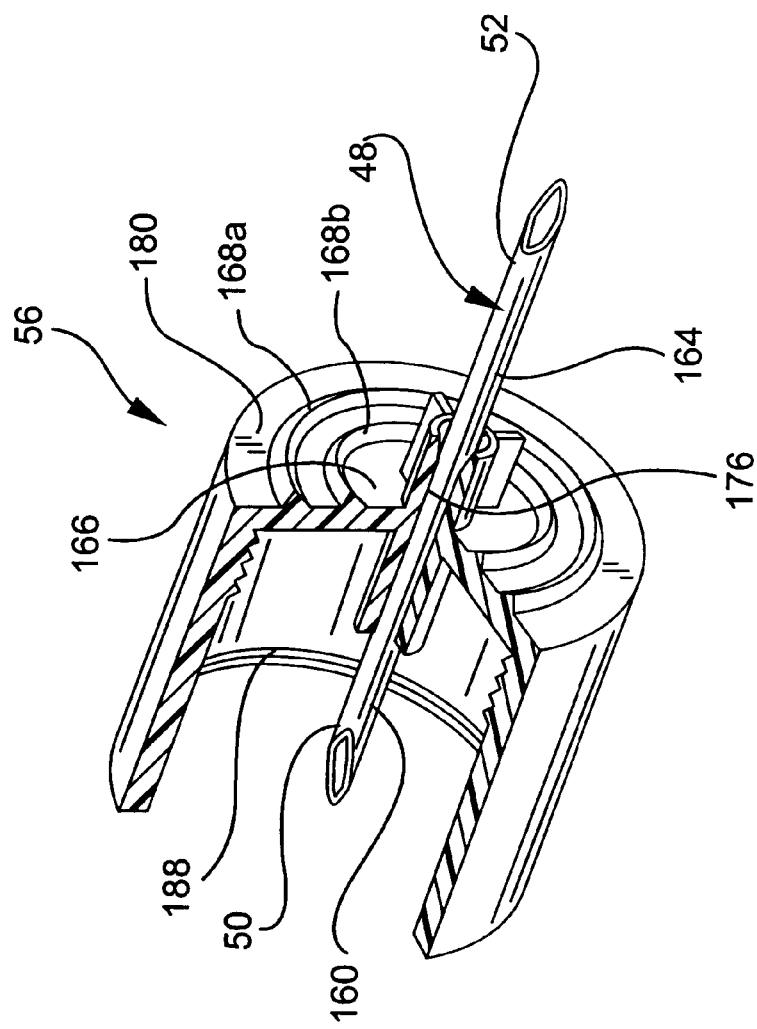
FIG. 2 is a partially cut-away view of a needle assembly in accordance with the present invention.

FIG. 2 is a partially cut-away perspective view of a needle assembly 46 in accordance with the present invention. Needle assembly 46 includes a needle cannula 48 and a needle hub 56.

The needle cannula 48 has opposed proximal and distal points 50 and 52, respectively and proximal and distal portions 160 and 164, respectively.

Hub portion 56 includes a cannula/hub interface 166 that is securely affixed at an intermediate position along shaft 176, which holds cannula 48. Hub 56 has a roof portion 180 with concentric raised ribs 168(*a*) ... (*n*) (where n is any suitable number). Although only two ribs are shown, any number of ribs could be used.

Ribs 168(*a*) ... (*n*) permit the needle cannula 48 to move about the centerline of the hub 56. Threads or camming surface 188 attach to threads on the cartridge retainer assembly (shown in FIG. 1 as 88). The needle cannula 48 typically has an outer diameter of approximately 0.009 inches to 0.018 inches and an inner diameter of approximately 0.0055 inches to 0.0120 inches. The needle cannula 48 is typically fabricated from materials such as stainless steel.

Figure 3:
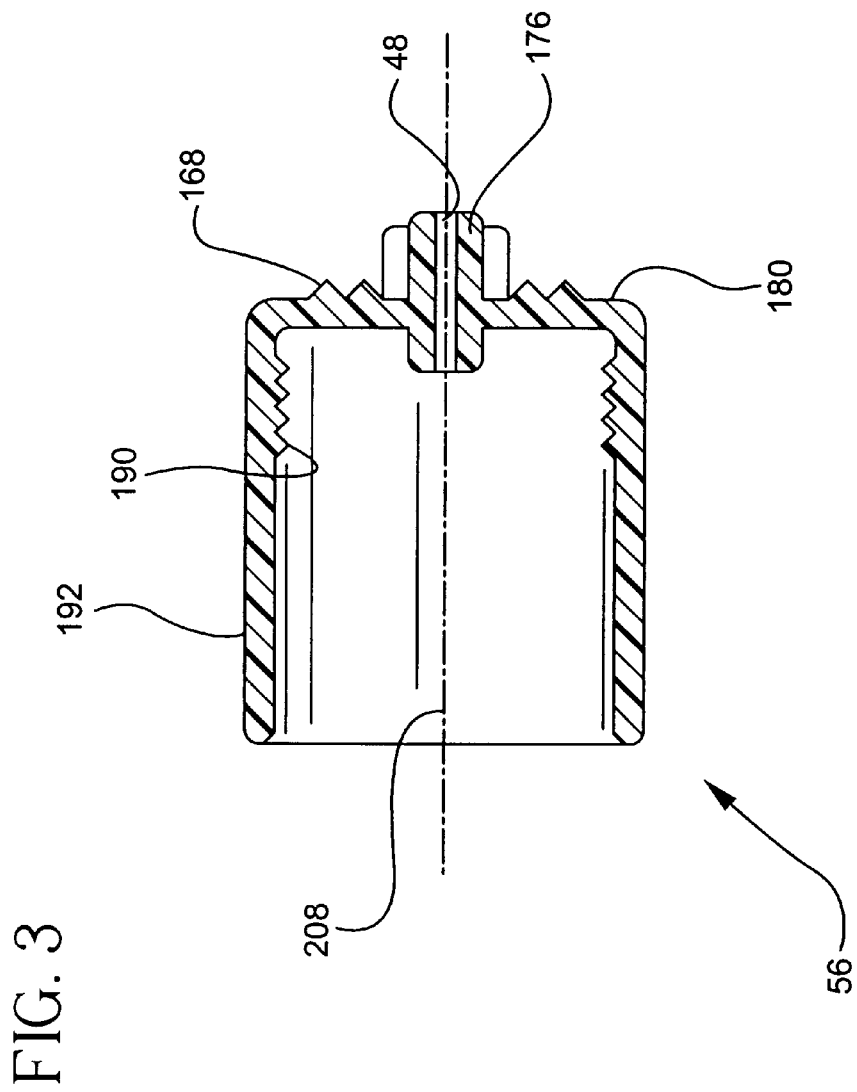
FIG. 3 is a cross-sectional view of a needle assembly in accordance with the present invention.

FIG. 3 shows a cross-sectional view along a longitudinal axis of the hub 56 that is attached to a cartridge retainer assembly (shown in FIG. 1 as element 10). Hub 56 is attached by camming surface 190 interfacing with a surface of wall 192, although other means of attachment could be used to connect hub 56 and cartridge retainer assembly. The needle cannula 48 is free to move with respect to the axial center line 208 of the hub 56. Flexibility is provided by concentric ribs, generally, 168 located on an area of the roof portion 180. Other flex means on the roof 180 of the hub 56 can be substituted in place of (or in combination with) the ribs 168. For example co-injection molded materials, ball-socket design, and an assembly of elastomeric materials, are suitably used instead of, or in addition to, ribs 168. Shaft 176 extends through roof 180, and provides support for needle cannula 48.

Figure 4:
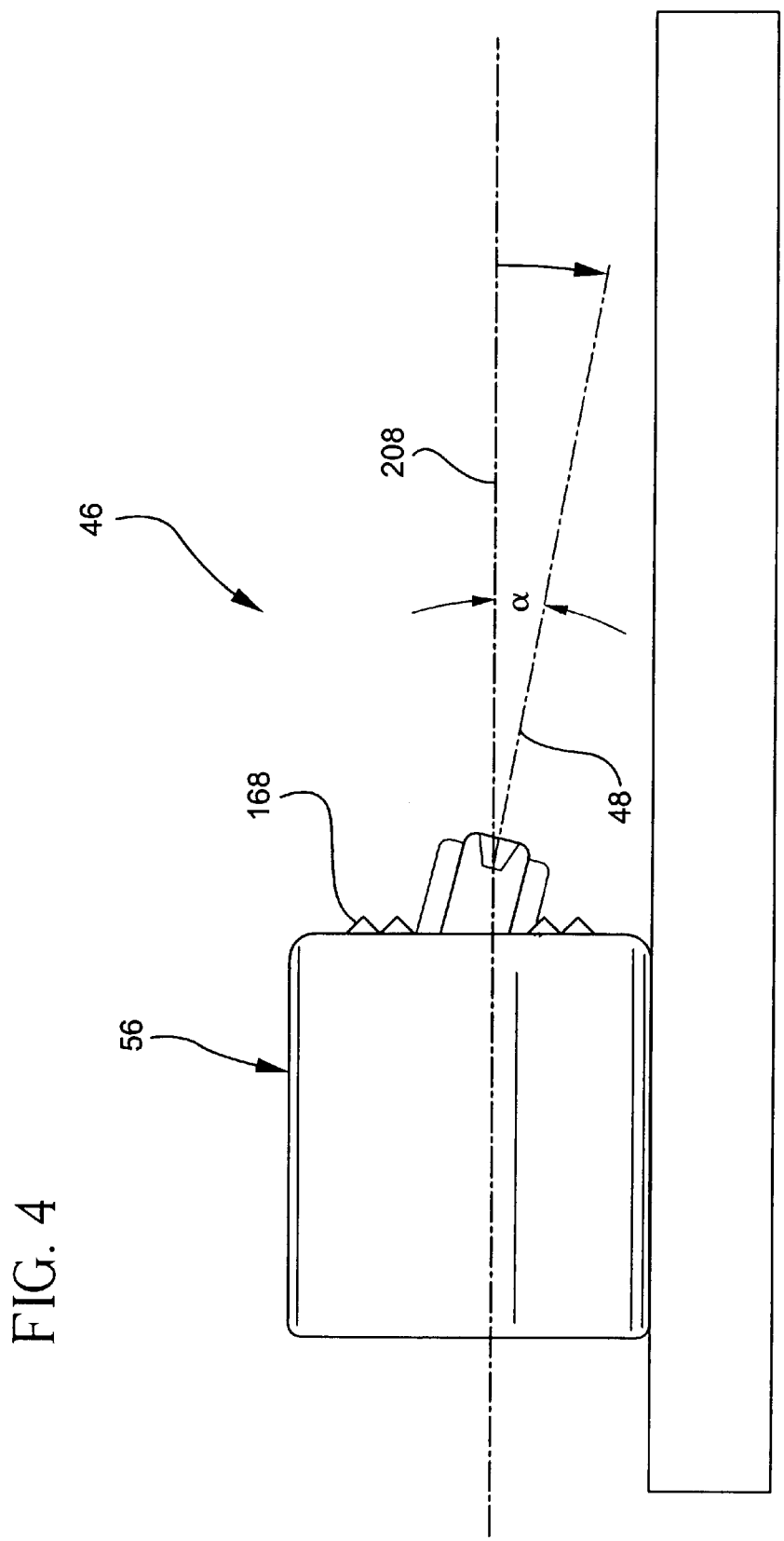
FIG. 4 shows the operation of a needle assembly in accordance with the present invention.

FIG. 4 shows a cross-sectional view of needle assembly 46. Flexible hub assembly 56 has concentric ribs 168 or other flexing means that permit the cannula 48 to move relative to the centerline 208 at an angle α. The angle α typically has a magnitude of approximately between 0–45 degrees. The flexing means can include a flexible roof portion 180 or ribs 168, which can be used in conjunction with the flexible roof portion or by themselves.

Figure 5:
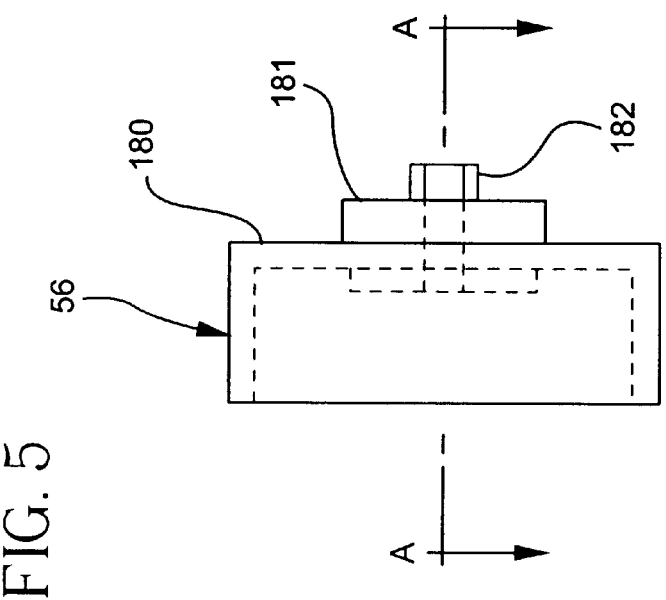
FIG. 5 shows a side view of the needle hub in accordance with the present invention.

FIG. 5 shows a side view of needle hub 56. In this embodiment, roof portion 181 is raised and fabricated from an elastomeric material that provides flexibility in a similar fashion as the ribs described herein. The raised roof portion 181 is at a plane different than the proximal surface 180 of the hub 56. This flexibility permits a needle cannula to move relative to a centerline. Support 182, which supports the cannula, is also shown. In this embodiment the raised roof portion 181 provides flexibility for a needle cannula (not shown). The flexible raised roof portion 181 can be used instead of, or in conjunction with, the ribs described herein.

Figure 6:
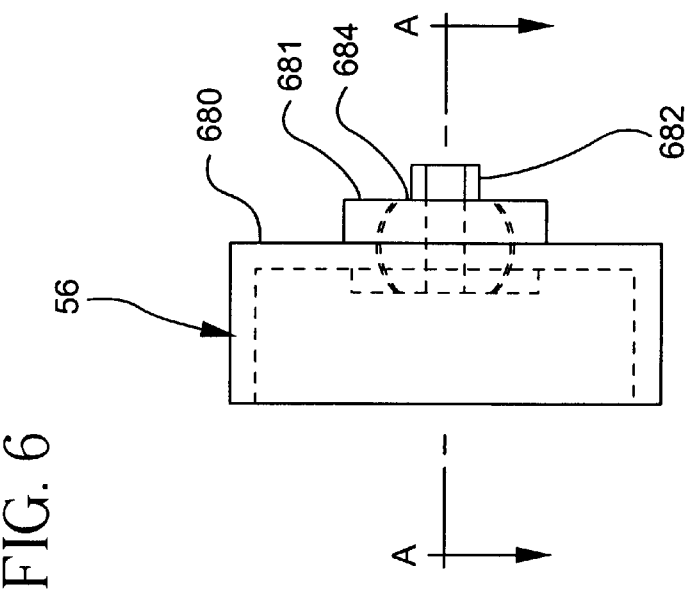
FIG. 6 shows a side view of the needle hub in accordance with a ball-and-socket embodiment of the present invention.

FIG. 6 shows a side view of the needle hub in accordance with the ball-and-socket embodiment of the present invention. Hub 56 has surface 680 upon which section 681, which forms a socket, is mounted. Shaft 682 extends from section 681 and rotational ball portion 684, which is connected to shaft 682, is disposed so as to form a ball-and-socket configuration with section 681. This ball-and-socket configuration permits the shaft 682 to hold a needle cannula (not shown in FIG. 6) such that the cannula rotates about the centerline of hub 56. As will be apparent to those skilled in the art, shaft portion 682 and rotational ball portion 684 could be fabricated as a single piece. They are labeled individually herein for explanation purposes.

Figure 7:
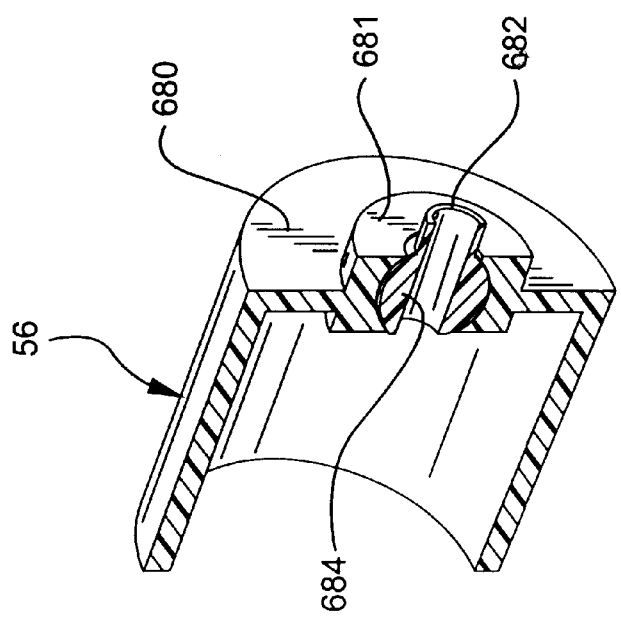
FIG. 7 shows a partial cut-away perspective view of the needle hub in accordance with the ball-and-socket embodiment of the present invention.

FIG. 7 shows a cut-away perspective view of the hub 56 in the ball-and-socket embodiment. Roof portion 680, socket portion 681, shaft 682 and rotational ball portion 684 are shown. Support 681 surrounds shaft 682 and provides a means to secure shaft 682 to roof portion 680. The ball-and-socket configuration enables rotation of the cannula about the centerline of the hub.

Figure 8:
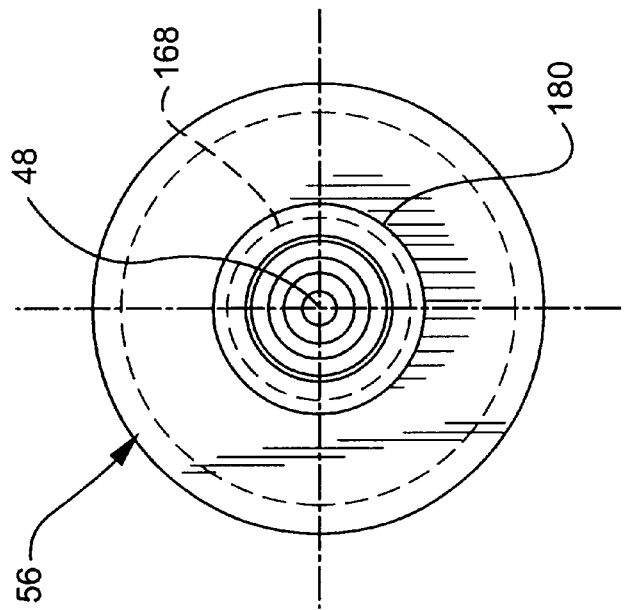
FIG. 8 shows an end view of the needle assembly in accordance with the present invention.

FIG. 8 shows an end view of the hub 56. Ribs 168 are disposed on roof portion 180. An end-view of needle cannula 48 is also shown.

The present invention has been described in detail by way of examples and illustrations for purposes of clarity and understanding, and not to in any way limit the scope of what is claimed. Those skilled in the art will understand that certain changes and modifications may be made without departing from the scope of the invention.

What is claimed is:

1. A needle assembly for use with a medication delivery pen, comprising:

a needle cannula having a proximal portion and a distal portion; and a hub, to which the needle cannula is mounted, the hub including a roof having a flexible roof portion, the flexible roof portion including one or more concentric ribs configured to permit the needle cannula to move about the centerline of the hub.

2. The needle assembly according to claim 1, wherein the hub comprises:

an interface disposed in the flexible roof portion through which the needle cannula is coupled to the hub.

3. The needle assembly according to claim 1, wherein the hub further comprises a threaded surface that engages a surface of the medication delivery pen.

4. A medication delivery system comprising:

a medication delivery pen;

a cartridge containing medication, the cartridge disposed within the medication delivery pen; and a needle assembly engageable with the cartridge, comprising:

a needle cannula having a proximal portion and a distal portion; and a hub to which the needle cannula is mounted, the hub including a roof having a flexible roof portion including one or more concentric ribs, wherein the flexible roof portion permits the needle cannula to move about the centerline of the hub, whereby the medication can flow through the needle cannula during an injection procedure.

5. The medication delivery system as claimed in claim 4, wherein the flexible roof portion is at a different plane than a proximal surface of the hub.

6. A method of operating a medication delivery system comprising the steps of:

attaching a needle cannula having a proximal portion and a distal portion to a hub, the hub including a roof having a flexible roof portion including one or more concentric ribs;

coupling the proximal portion of the needle cannula to a cartridge containing medication;

disposing the cartridge within a medication delivery pen;

injecting the distal portion of the needle cannula into a patient; and delivering the medication into said patient, whereby the flexible roof portion permits the needle cannula to move about the centerline of the hub.

* * * * *